United States Patent
Wardlaw et al.

(10) Patent No.: US 6,350,613 B1
(45) Date of Patent: Feb. 26, 2002

(54) DETERMINATION OF WHITE BLOOD CELL DIFFERENTIAL AND RETICULOCYTE COUNTS

(75) Inventors: Stephen C. Wardlaw, Old Saybrook; Robert A. Levine, Guilford, both of CT (US); Rodolfo R. Rodriguez, Cary, NC (US)

(73) Assignee: Belton Dickinson & Co., Franklin Lakes, NJ (US)

( * ) Notice: Subject to any disclaimer, the term of this patent is extended or adjusted under 35 U.S.C. 154(b) by 0 days.

(21) Appl. No.: 09/252,153

(22) Filed: Feb. 18, 1999

Related U.S. Application Data

(60) Provisional application No. 60/077,207, filed on Mar. 7, 1998.

(51) Int. Cl.[7] .................... G01N 31/00; G01N 33/48
(52) U.S. Cl. .................... 436/10; 436/8; 436/63; 436/164; 436/172; 435/2; 422/55; 422/58; 356/39; 356/244; 356/246
(58) Field of Search .................... 436/8, 10, 18, 436/63, 164, 165, 172, 174; 435/2, 4, 29, 30, 39; 422/55, 58, 99, 102; 356/39, 244, 246

(56) References Cited

U.S. PATENT DOCUMENTS

| | | | | |
|---|---|---|---|---|
| 4,125,828 A | * | 11/1978 | Resnick et al. | 382/134 |
| 4,146,604 A | * | 3/1979 | Kleinerman | 435/40.51 |
| 4,790,640 A | * | 12/1988 | Nason | 359/396 |
| 4,950,455 A | * | 8/1990 | Smith | 422/56 |
| 5,427,959 A | | 6/1995 | Nishimura et al. | 436/534 |
| 5,547,849 A | * | 8/1996 | Baer et al. | 435/7.24 |
| 5,585,246 A | * | 12/1996 | Dubrow et al. | 435/7.24 |
| 5,932,428 A | * | 8/1999 | Dubrow et al. | 435/7.24 |
| 5,948,686 A | * | 9/1999 | Wardlaw | 436/63 |
| 6,235,536 B1 | * | 5/2001 | Wardlaw | 436/172 |

* cited by examiner

Primary Examiner—Maureen M. Wallenhorst
(74) Attorney, Agent, or Firm—William W. Jones

(57) ABSTRACT

Target nucleated cells, and target cells containing remnant ribosomal material, which are present in a quiescent anti-coagulated whole blood sample are optically detected, enumerated, and analyzed in a sample chamber that has a varying through plane thickness due to convergent opposing sample chamber walls. At least one of the convergent walls of the chamber is transparent so that the blood sample can be observed. The chamber's varying thickness produces a first lesser thickness region in the chamber wherein individual red cells and quiescent monolayers of red cells in the sample will reside after the sample is introduced into and fills the chamber. Larger formed constituents such as white blood cells and nucleated red blood cells present in the sample will reside in greater thickness regions of the chamber, and non-nucleated red cells which reside in such greater thickness regions will agglomerate to form rouleaux. By admixing fluorescent dyes with the blood sample, target cells in the sample can be enumerated and differentiated by means of a scanning instrument which is able to measure different wave length color signals emitted from the target cells in the sample, and differentiate the target cells one from another by reason of the nature of the emitted color signals.

23 Claims, 4 Drawing Sheets

DETERMINATION OF WHITE BLOOD CELL DIFFERENTIAL AND RETICULOCYTE COUNTS

This application claims the benefit of U.S. Ser. No. 60/077/207, filed Mar. 7, 1998.

TECHNICAL FIELD

This invention relates to an apparatus and method for analyzing a quiescent sample of anticoagulated whole blood. More particularly, this invention relates to an apparatus and method for analyzing the blood sample in a quiescent state in order to provide a white blood cell differential count, a reticulocyte count analysis, an enumeration of nucleated red blood cells, and the ability to detect abnormal nucleated circulating cells, such as cancer cells, which are rare events.

BACKGROUND ART

Recent advances in analytical hematology have increased the quantity and quality of information available from a patient's blood sample. As a result, the medical community's interest in using patients' blood samples as a diagnostic tool has also increased, with the most commonly performed test performed on anticoagulated whole blood being the complete blood count, or CBC, which is a suite of tests which may include, in addition to the enumeration of the cellular components and platelets, red blood cell metrics; reticulocyte counts; and the leukocyte differential count (LDC or "Diff") which is the classification of the types of white blood cells present in the blood sample. The general physical properties of the sample, namely various cell or counts must be analyzed using quantitative methods relating to the entire sample. In conventional instrumentation and methods, this requires accurate sample metering and dilution, followed by specialized measurement apparatus. Additionally, the instrument must measure quantitative aspects of the individual cells, which usually involves providing a high dilution of the sample with a subsequent passage of the diluted material through a flow cell which measures the cells using electrical or optical means. Still further, qualitative measurements are used to classify the percentage of the total white blood cells which are composed of specific sub populations. The number of sub-populations depends upon the sophistication of the instrument involved, which may be as little as two or more than seven classifications.

Historically, the differential aspects of the CBC have been performed using separate methods from those used for enumeration. For example, the LDC portion of a CBC was traditionally performed by smearing a small amount of undiluted, blood on a slide, staining the dried, fixed smear, and examining the smear under a microscope. Reasonable results can be gained from such a smear, but the accuracy and reliability of the data depends largely on the technician's experience and technique. One problem with such smears is that the cells must be killed and fixed, and this precludes many types of supravital stains and analyses whose results depend upon the living cell, such as some cytochemical analyses. In addition, the use of blood smears is labor intensive and cost prohibitive, and is therefore generally not favored for commercial applications.

Another method of performing an LDC uses electrical impedance or optical flow cytometry. Flow cytometry involves passing a diluted blood sample through a small vessel wherein electrical impedance or optical sensors can evaluate the constituent cells as they pass serially through the vessel. The same apparatus may also be used to simultaneously enumerate and provide cell metric data. To evaluate WBC'S, the blood sample must be diluted, and the sample must be treated to mitigate the overwhelming number of the RBC's relative to the WBC'S. Although more expedient and consistent than the above described smear methods, flow cytometry also possesses several disadvantages. One disadvantage of flow cytometry is the plumbing and fluid controls that are necessary for controlling the flow rate of the diluted blood sample past the sensors. The plumbing in current flow cytometers can, and often does, leak, thus potentially compromising the accuracy and the safety of the equipment. These analyses are also generally incapable of providing any type of morphometric analysis, since an actual image of each cell is not obtained; only the total signal from any given cell may be analyzed. Another disadvantage of many current flow cytometers relates to the accuracy of the internal fluid flow controls and automated dilution equipment. The accuracy of the flow cytometer depends upon the accuracy of the fluid flow controls and the sample dilution equipment, and their ability to remain accurately calibrated. Flow controls and dilution equipment require periodic recalibration. The need for recalibration illustrates the potential for inaccurate results and the undesirable operating costs that exist with many presently available flow cytometers. An article authored by John L. Haynes, and published in *Cytometry Supplement* 3: 7–17 in 1988 describes the principles of flow cytometry, both impedance and optical, and the application of such a technology to various fields of endeavor. Blood samples being examined in flow cytometers are diluted anywhere from 10:1 to 50,000:1.

Another approach to cellular analysis is volumetric capillary scanning as outlined in U.S. Pat. Nos. 5,547,849; 5,585,246 and others, wherein a relatively undiluted sample of whole blood is placed into a capillary of known volume and thickness and is examined while the blood is in a quiescent state. This technique deals with the presence of the red blood cells by limiting the scanning wavelengths to those to which the red blood cells are relatively transparent, and it requires that the sample be treated so that the red blood cells do not aggregate during the measurement process. Thus, this technique is limited to the use of longer wavelength fluorescence, and there is no provision for the enumeration of reticulocytes or nucleated red blood cells. Additionally, as with flow cytometry, no morphologic information is available from the scans. There are a number of commercial instruments available for performing a CBC or related tests, but those which provide more than a few of the CBC tests quickly become complex, expensive and prone to malfunction. In addition, there are a number of methods proposed for specific hematological tests, but these do not provide all of the clinically useful information which is expected in a CBC.

All of the above methods are generally limited to a single mode of analysis, in that a combination of histochemical staining and cellular morphology is not possible. Having the capability to perform both of these types of tests expands the number of groups which can be recognized by the method.

It would be desirable to have a method and apparatus for examining a quiescent sample of anticoagulated whole blood, which method and apparatus are capable of providing accurate results for a LDC, reticulocyte enumeration and detection of nucleated red blood cells and abnormal circulating nucleated cells, such as cancer cells, and does not require sample fluid flow through the sampling chamber during sample analysis.

DISCLOSURE OF THE INVENTION

This invention relates to a method and apparatus for use in examining and obtaining information from a quiescent substantially undiluted anticoagulated whole blood sample which is contained in a chamber. The phrase "substantially undiluted" as used in connection with this invention describes a blood sample which is diluted by no more than about 1:1, and preferably much less. Generally the only reagents that will be used in performing the method of this invention are dyes, stains and anticoagulants, and these reagents, even if liquid, are not designed to dilute the specimen. The analysis may be performed within a chamber having a fixed depth, as long as the depth supports the formation of red blood cell aggregations and lacunae, which form in a layer having a thickness from about seven to about forty microns, depending upon the hematocrit of the sample. However, having a fixed depth makes it more difficult to analyze samples having a widely varying white cell count, and the simultaneous enumeration of reticulocytes is impossible in this type of chamber. Preferably, a chamber is used which has a varying through plane thicknesses as described below. The several regions in the chamber will create sufficient capillary forces in all regions of the chamber so as to cause spreading of the blood sample throughout the chamber, which ultimately results in a quiescent blood sample in the chamber. The only motion in the blood sample at the time of analysis will be Brownian motion of the blood sample's formed constituents, which motion is not disabling of the utility of this invention. The apparatus includes a sample-holding chamber which has opposite sample-containment walls, at least one of which is transparent, which walls preferably converge in at least one portion of the chamber. In the preferred embodiment, the through plane thickness of the chamber thus varies in different regions of the chamber. As used in this disclosure, the phrase "through plane" refers to a line of sight which corresponds to the shortest distance between the convergent walls in any region of the chamber. The degree of convergence of the two walls, i.e., the distance between the two walls, at any particular point in the chamber is either known, or it can be measured after the sample has been placed in the chamber, as will be described hereinafter.

The thinnest region in the chamber will be sized so that a monolayer of individual red blood cells present in the sample will form when the chamber is filled with the blood sample. The thickness of this region of the chamber should be between about two and about seven microns, and is preferably about five microns. Thus measurements of red cells' differential reticulocyte counts can be derived in this region of the chamber.

From the thin portion of the chamber, the chamber thickness increases so as to form progressively thicker regions in the chamber that are used to differentiate and differentially enumerate various white cell types and nucleated red blood cells in the blood sample. The nucleated red blood cells tend to be about the size of small lymphocytes, but can be larger. The thickness of the chamber in this region thereof is typically in the range of between about seven to about forty microns. The chamber is contained in a sample holder into which the blood sample can be drawn.

The sample to be assayed is admixed with a colorant which can be, for example, a fluorescent dye or dyes, and the resultant admixture spreads out in the chamber so as to form a quiescent sample that has a varying thickness due to the convergence of the walls of the chamber. The colorant(s) can be added to the sample prior to admission of the sample into the chamber, or the colorant can be added to the sample while the sample is within the confines of the chamber, such as by dry coating the colorant on walls of the chamber. Regions of interest in the chamber are selectively illuminated by a light source having a selected wavelength, or wavelengths, which causes the colorant in the sample to fluoresce. Regions in the chamber containing the red cell monolayers and the white cells and red cell rouleaux in the blood sample are thus scanned, preferably by an optical instrument, and the results of the scans may be digitized and analyzed. Differential platelet counts with platelets grouped by size and RNA content, as determined by fluorescence, can also be derived in the region of the chamber wherein the red cell rouleaux and lacunae form. Platelets with increased RNA are younger platelets.

This invention provides a method for performing at least a three part differential white blood cell count in a sample of anticoagulated whole blood, which method includes the steps of: providing a sampling chamber that is dimensioned so as to enable the aggregation of the red blood cell population and the separation of individual white blood cells from the red cells in a substantially undiluted anticoagulated whole blood sample which is introduced into the chamber. An admixture of a fluorescing colorant or colorants and the anticoagulated whole blood sample is formed in the sampling chamber. The colorant or colorants are operable to differentially highlight at least three different white blood cell types in the whole blood, and preferable five different white blood cell types. The admixture is allowed to disperse through the chamber so as to form separated quiescent groups of one or more individual white blood cells within open lacunae of plasma in optical working fields in the sample. It should be understood that the white blood cells are by in large excluded from the mass of the red blood cells as the latter aggregate. However, for the purposes of this invention, the white blood cells may lie on top of individual red blood cells of the red cell aggregates and still be detected and evaluated as long as the white cells are visible to the scanning instrument. The fields are optically scanned by performing a field-by-field X-Y-Z scan of the dispersed admixture in the chamber under suitable lighting conditions that will cause at least three and preferably five or more different white cell types to be differentially highlighted by said colorant or colorants. All of the differentially highlighted cells which are detected in the admixture are enumerated, and the enumerated cells are grouped by cell type. The same colorants and light conditions can be used to perform reticulocyte or nucleated red blood cell counts in the blood sample due to the presence of nuclear material in the cells. In the case of the reticulocytes, the nuclear material in the cells constitutes remnants of the cells' nucleus, such as intracellular RNA, and in some cases intracellular DNA. The differentially fluorescing intracellular material present in reticulocytes can be characterized as "remnants of intracellular nucleated material". The reticulocyte and non-nucleated red cell parameter analyses are performed in the thinnest region of the chamber where individual mature red cells and monolayers of mature red cells, as well as reticulocytes can be expected to be found due to their size.

It is therefore an object of this invention to provide a method and apparatus for use in obtaining differential blood cell counts of certain nucleated blood cells and platelets in a quiescent anticoagulated whole blood sample.

It is an additional object of this invention to provide a method and apparatus of the character described which enables a substantially undiluted whole blood sample to be examined for differential white blood cell subpopulation counts; total white cell subpopulation counts; reticulocyte counts; nucleated red blood cell counts; platelete counts; and detection of abnormal nucleated circulating cells, such as cancer cells.

BRIEF DESCRIPTION OF THE DRAWINGS

These and other objects and advantages of the invention will become more readily apparent from the following detailed description of several embodiments of the invention when taken in conjunction with the accompanying drawings in which.

DETAILED DESCRIPTION OF SPECIFIC EMBODIMENTS OF THE INVENTION

Figure 1:
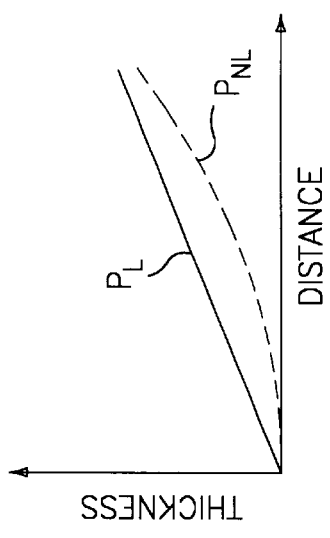
FIG. 1 is a schematic perspective view of a blood sample-analyzing device which includes a sample-receiving chamber, which chamber includes varying through plane thickness regions.

Referring now to the drawings, FIG. 1 is a schematic illustration of a device which is denoted generally by the numeral 2, which device 2 includes a sample containing chamber 14 that has a varying through plane thickness. The device 2 includes a lower support wall 4, which for illustrative purposes may, for example, be a microscope slide. The device may also include a rectilinear shim 6; and an upper wall 8, which for illustrative purposes may, for example, be a microscope slide cover slip. At least one of the walls 4 and 8 must be transparent so that the sample disposed therebetween can be examined through the transparent wall 4 or 8. If so desired, both of the walls 4 and 8 can be transparent. The wall 8 has one edge 10 which rests on, or very near, the wall 4, and an opposite edge 12 which is disposed an the upper surface of the shim S. The result of the convergent relationship between the walls 4 and 8 is the formation of a chamber 14 that has a varying through plane thickness, the through plane thickness increasing from the edge 10 to the opposite edge 12 of the wall 8, as will be seen in FIG. 1.

Figure 2:
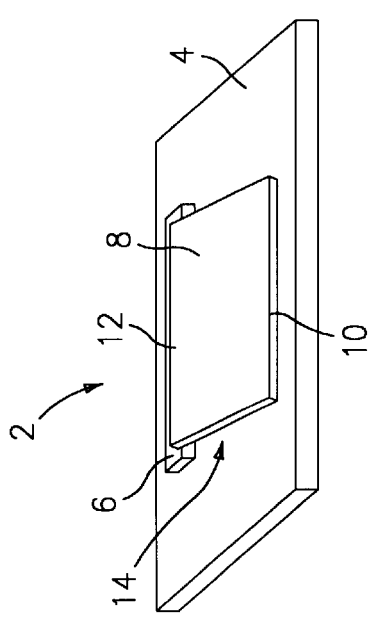
FIG. 2 is a plot of the relationship between chamber thickness and the distance from the smallest through plane thickness region in the chamber to any other through plane thickness region in the chamber, with the solid trace being representative of a linear chamber such as that shown in FIG. 1 and the broken trace being representative of a non-linear varying thickness chamber.

FIG. 2 is a graphic representation showing how the thickness of the chamber 14 can vary from the thinnest edge 10 to the thickest edge 12. The solid line $P_L$ shows a thickness-distance relationship created by a chamber configuration which is linear; and the broken line $P_{NL}$ shows a thickness-distance relationship created by a chamber configuration which is non-linear.

Figure 3:
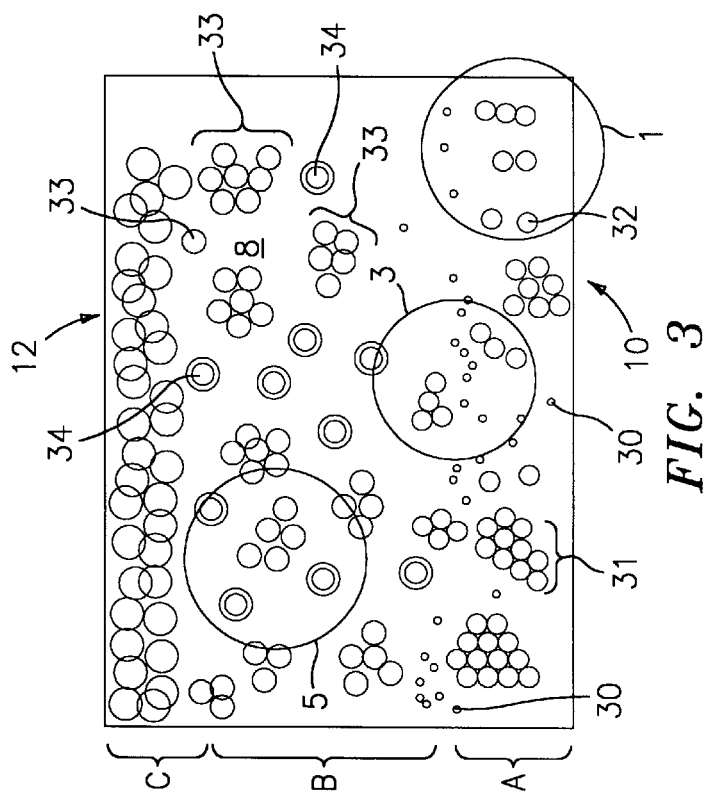
FIG. 3 is a schematic plan view of a portion of a varying thickness chamber formed in accordance with this invention and illustrating in a schematic sense how the various size formed constituents in a quiescent blood sample will separate into the various thickness regions in the chamber so as to be individually visible in different fields of view in the chamber.

FIG. 3 is a schematic representation of a plan view of the device 2 which incorporates the chamber 14, and of the manner in which any differently sized formed constituents present in the blood sample being examined will quiescently distribute in the chamber 14 when the latter is filled with the sample. The numeral 10 indicates a lesser thickness region of the chamber 14, and the numeral 12 indicates a greater thickness region of the chamber 14. In the representation of the device 2 shown in FIG. 3, there are three different thickness regions, A, B and C in the portion of the chamber 14 depicted. Region A is a lesser thickness region in the chamber 14; region B is a medium thickness region in the chamber 14; and region C is the largest thickness region in the chamber 14. Obviously, this particular number of different thickness regions is used merely to illustrate a primary feature of the preferred chamber 14 of this invention, and is not limiting of the invention, since the chamber 14, as noted above, can include an essentially infinite number of different thickness regions. There are also three different fields of view 1, 3 and 5 shown in the FIG. 3. These fields of view 1, 3 and 5 are depicted as circles so as to illustrate the field of view as seen by an optical instrument, such as a microscope. In the illustration depicted in FIG. 3, the blood sample has filled the chamber 14 and has been quiescent for at least a few seconds. In the thinnest region A of the chamber 14 are found flattened red blood cells, either singly 32, or in a monolayer 31. A few platelets 30 may also be found in the region A. Reticulocyte and non-nucleated red blood cell counts can be performed in the region A of the chamber 14, as described hereinafter.

In the lower part of region B, there is sufficient room for the red blood cells to form rouleaux or other aggregates 33 which are surrounded by plasma lacunae that are free of the red blood cells due to the rouleaux formation. In field of view 3 there is sufficient chamber volume to allow the enumeration and classification of the white blood cells 34 and also of nucleated red blood cells. The white blood cells 34 can thus be assayed in this region for surface receptor sites; can be typed; can be volumetrically measured; can be morphologically studied; and additional bits of information about the white blood cells 34 can be derived from the blood sample in the upper part of the region B. As the chamber thickness increases to that shown in region C, the red blood cell agglomerates 33 form a confluent layer, and the ability to locate white blood cells is reduced, although this region may be utilized for very low white cell counts.

Figure 4:
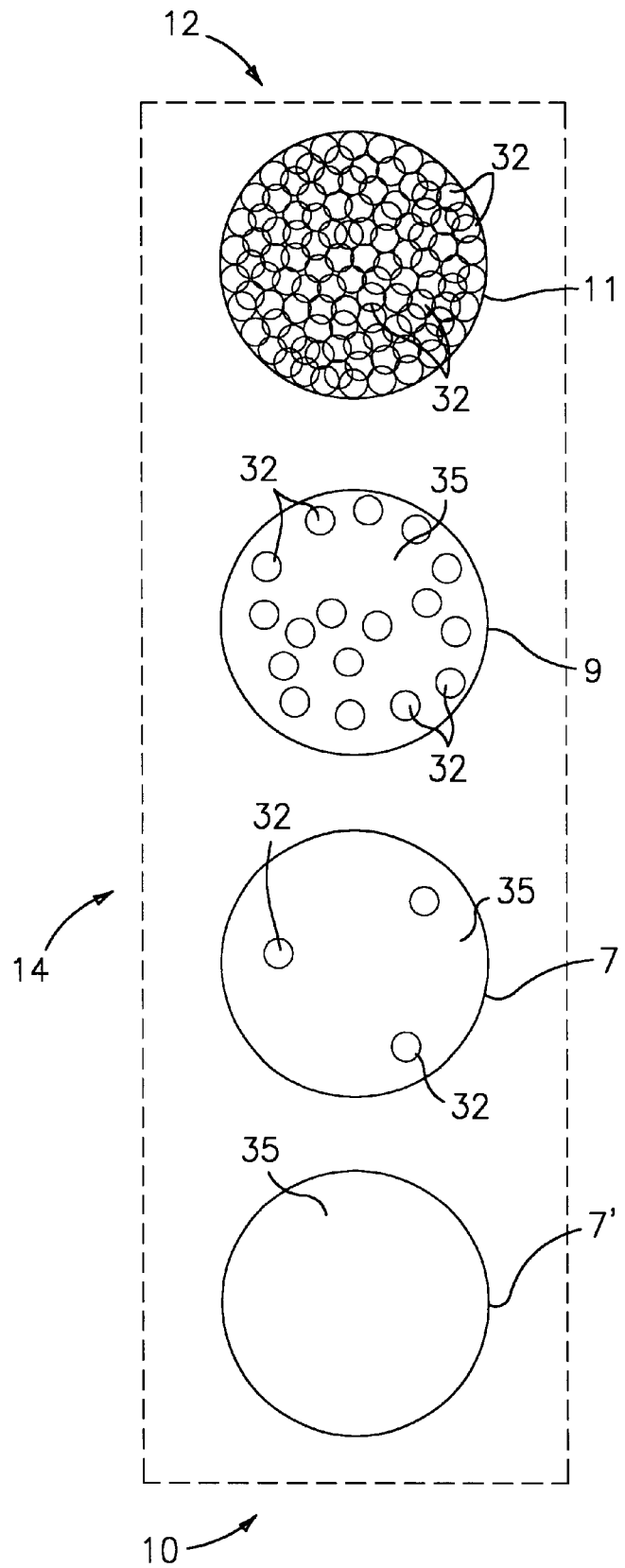
FIG. 4 is a schematic plan view of a portion of the chamber showing four different fields of view that might be surveyed by a sample-scanning instrument.

FIG. 4 is a plan view of a fragment of the chamber 14, wherein the numeral 12 indicates a thicker end of the chamber 14 and the numeral 10 indicates a thinner and of the chamber 14. A chamber 14 having a varying thickness which varies from about zero microns at its thinnest portion 10, to about two hundred microns at its thickest portion 12, will allow a one hundred fold dynamic range of blood sample particulate counts-per-unit-volume of sample. There are four schematic fields of view 7', 7, 9 and 11 shown in FIG. 4. Formed constituents 32 are depicted in each of the fields of view 7, 9 and 11, and none is shown in the field of view 7'. Lacunae 35 are also depicted in fields of view 7', 7 and 9, but not in field 11.

Figure 5:
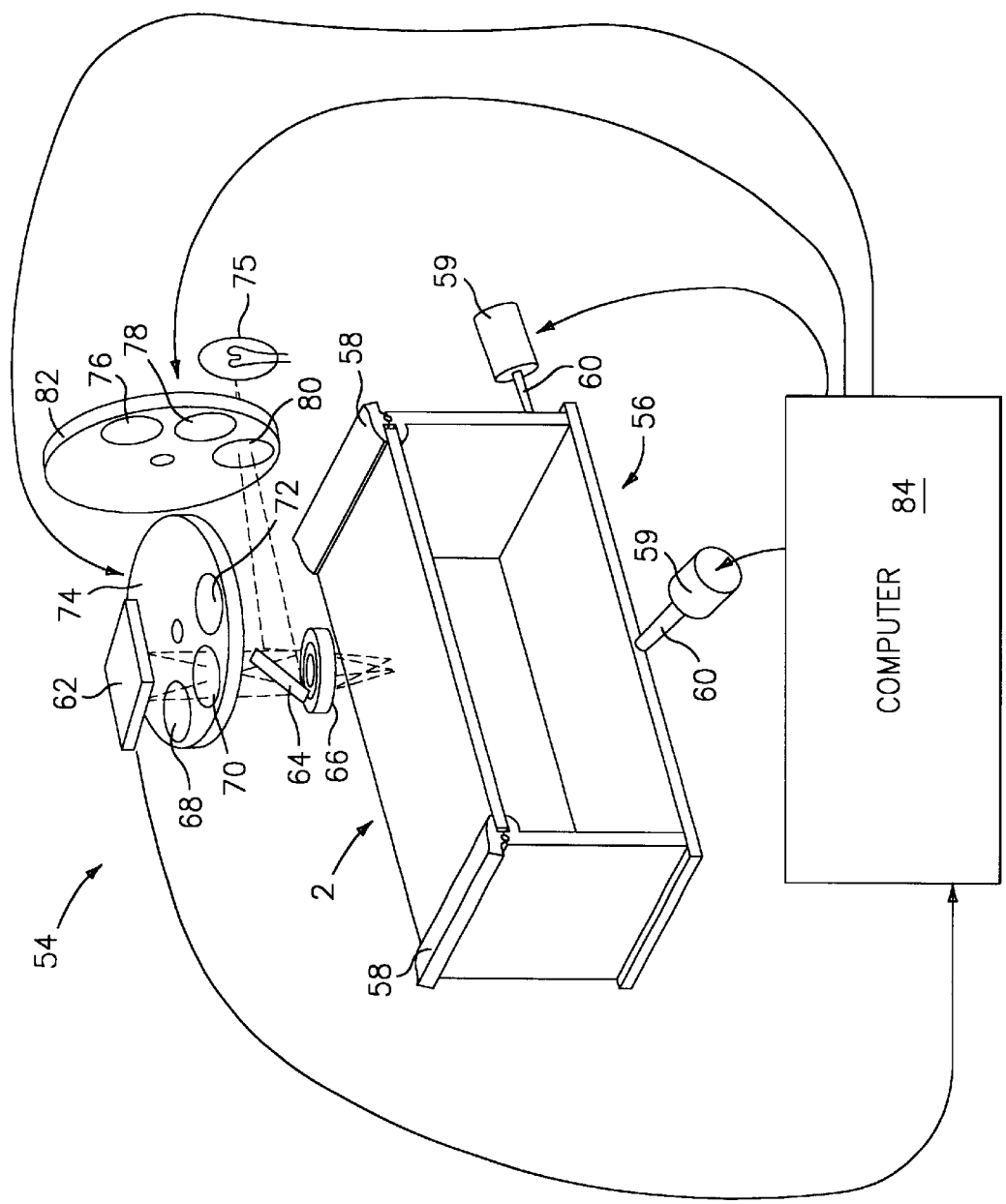
FIG. 5 is a schematic view of a scanning instrument which can be used to identify, count and analyze certain characteristics of the formed components of an anticoagulated whole blood sample placed in the chamber.

FIG. 5 is a schematic depiction of an automated colorimetric microscopical instrument assembly which is denoted generally by the numeral 54, and can be used to scan a blood sample that is contained in the device 2, and can, without significant human intervention, colorometrically analyze wavelengths of color emissions from different white cell types, reticulocytes and nucleated red cells in the blood sample, thereby identifying and differentiating these cell types one from another. The instrument assembly 54 is designed to create and store or transmit the images of different white cells types, reticulocytes and nucleated red cells in the blood sample being scanned. The instrument assembly 54 includes a stage 56 which includes clips 58 that engage the sample holder 2, and enables the sample holder 2 to be moved transversely in the X and Y directions as the contents of the sample holder 2 are scanned.

Reversible electric motors 59 can be used to selectively rotate drive screws 60 in opposite directions so that the sample holder 2 can be transversely moved in the X and Y directions. In this manner, the entire contents of the sample holder 2 can be scanned. The automatic embodiment of the disclosed instrument assembly 54 includes a CCD camera 62, a beam splitter 64, and lens 66 set which can be selectively moved in the Z direction so as to focus upon the sample-containing portions in the sample holder assembly 2. The CCD camera 62 may view and record images of the sample through a plurality of different emission light wave filters 68, 70 and 72 which may be mounted on a selectively rotatable filter wheel 74. The instrument assembly 54 also includes a high intensity excitation light source 75, such as a halogen light source, which directs an excitation light beam at the sample holder 2 through the beam splitter 64 and the focusing lens set 66. A series of excitation light wave length filters 76, 78 and 80 may be mounted on a selectively rotatable filter wheel 82. The excitation light beam is deflected by the beam splitter 64 toward the focusing lens 66, and is focused on the sample holder 2 by the lens 66. Thus, the two filter wheels 74 and 82 can allow one to selectively control and vary the wave lengths of the excitation light source, as well as the emitted light source. A pre-programmed processor controller 84 is operable to selectively control movement of the sample holder 2; the rotation of the filter wheels 74 and 82; and operation of the CCD camera 62. The controller 84 thus enables fully automatic operation of the instrument assembly 12 without the need of significant human intervention.

As noted above, as the scanning instrument searches the chamber 14 for useful regions in the chamber 14 in performance of an examination of the sample which involves deriving differential counts of white blood cells, reticulocytes and nucleated red blood cells in the chamber 14, it will see fields of view such as 7', 7, 9 and 11, as shown in FIG. 4.

When the scanning instrument has surveyed a clinically significant number of useful cells, it will complete the differential white cell differential analysis, and the reticulocyte and nucleated red cell analysis. The determination of what constitutes a statistically significant number of counted constituents will depend upon a predetermined clinically acceptable margin of error for the counting procedure. It will be appreciated that this number will vary depending on what constituents are being counted.

White blood cells, nucleated red blood cells, and reticulocyte cells that contain ribosomal remnants of nuclear material, which cells are present in the sample and which are supravitally stained with a colorant, such as basic orange 21, may be identified by virtue of the cells' characteristic fluorescence at 530 nm, 585 nm and 660 nm when excited by light in the 485 nm range, and by their fluorescence at 610 nm when excited by light of 560 nm. The quiescent white cells can be separated by the instrument 54 into differentiated groups consisting of lymphocytes, monocytes, granulocytes, eosinophils and basophils in said chamber. Other dyes such as acridine orange may be used with similar wavelengths to perform a similar analysis.

The preferred method for classifying or differentiating the various blood cells is as follows. Multiple fields containing white blood cells, and which may also contain large nucleated red blood cells, are illuminated with an excitation wavelength of 485 nm, and the white blood cells and any nucleated red blood cells are located. The location algorithm relies on the fact that the white blood cells and some large nucleated red blood cells are the only large objects in any field which fluoresce. The required number of white blood cells are located, and five emission values are recorded, wherein: $L_1$, $L_2$ and $L_3$ are the total emission from each cell at 530 nm, 580 nm and 660 nm respectively, and where the total emissions are measured by summing the intensities of the pixels from the cell images; $AL_1$ is the average pixel intensity of each cell at 530 nm when excited at 485 nm; $AL_5$ is the average pixel intensity measured for each cell at 610 nm when the cell is excited with light at 560 nm; and $A_{580}$ is the area of the cell as determined by the emission at 580 nm when excited at 488 nm. Thus, the data used to differentiate the cell types includes photometric data ($L_1$, $L_2$, $L_3$) as well as morphometric data ($AL_1$, $AL_5$, $A_{580}$).

Figure 6:
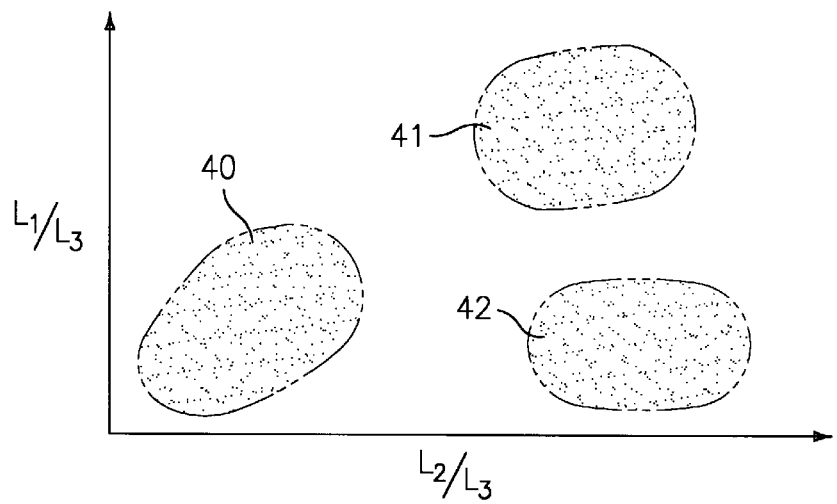
FIG. 6 is a two dimensional plot showing the clustering of white blood cell groups under a specific set of analysis conditions.

FIG. 6 shows the cells imaged by the instrument 54 as displayed in two-dimensional space, where the Y axis is the ratio of $L_1/L_2$, and the X axis is the ratio $L_2/L_3$. Using cluster analysis, the cells are grouped into three populations, where cluster 40 represents the neutrophils and eosinophils, cluster 41 represents the monocytes and lymphocytes, and cluster 42 represents the basophils. These are the types of cellular separations based upon photometric data alone. To get a more finite separation, the addition of morphometric data will further subdivide the clusters so as to allow the identification of more cell types.

Figure 7:
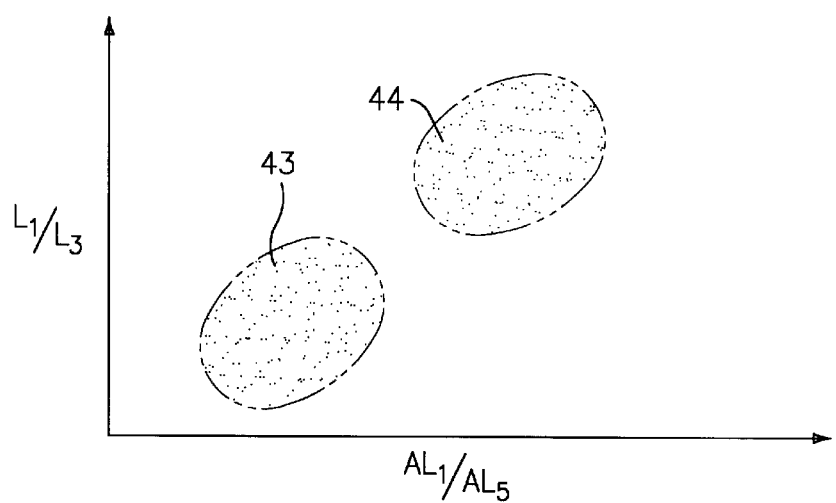
FIG. 7 is a two dimensional plot showing the sub-grouping of one of the clusters of FIG. 6 under a second set of analysis conditions.

FIG. 7 shows the cluster 40 which is now subjected to a further two-dimensional cluster analysis, where the X axis is the ratio of $AL_1/AL_5$, and the Y axis is the ratio $L_1/L_3$. This cluster analysis now allows the division of the original cluster 40 into two separate clusters representing the eosinophils 43 and the neutrophils 44.

Figure 8:
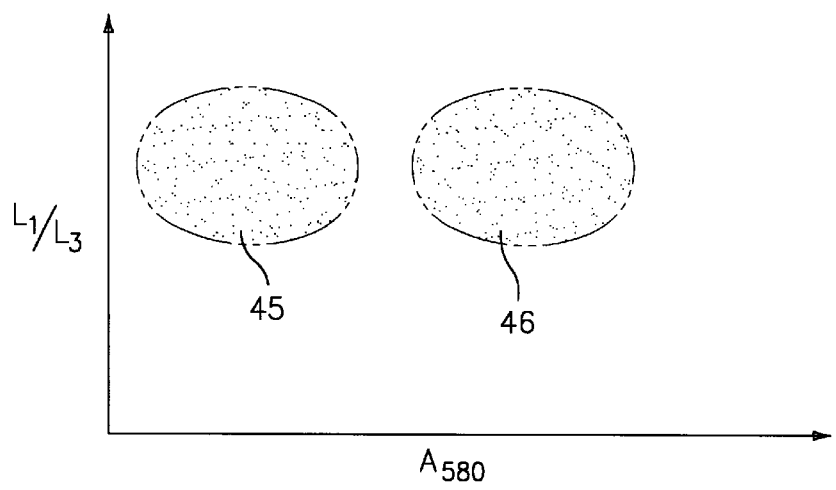
FIG. 8 is a two dimensional plot showing the sub-grouping of one of the clusters of FIG. 6 under a third set of analysis conditions.

If cluster 41 is subjected to additional cluster analysis as shown in FIG. 8, where the X axis is $A_{580}$ and the Y axis is the ratio $L_1/L_3$, cluster 41 may be separated into its two components, the monocytes 46 and the lymphocytes 45. Thus, the steps described above are capable of subdividing a white blood cell population into at least five sub-groups. The different types of white cells identified and enumerated are typically recorded as percentages of the total number of white cells scanned during the procedure.

The presence of the reticulocytes within the red blood cell population is determined by measuring the total intensity of the 585 nm and 660 nm fluorescence from each red blood cell when excited at 485 nm, and those cells which have a higher total fluorescence than those of normal red blood cells are determined to be reticulocytes. Similarly, those red blood cells which show a strong fluorescence at 530 nm are considered to be nucleated red blood cells.

The above examples have used supravital stains which give an indication of the general character of the cells, but it is also possible to use specific epitopic binding agents, such as antibodies, which may be labeled with fluorescent dyes, or labeled with colored or fluorescent particulates. These can serve to further separate sub-populations of the nucleated cells based on surface antigens or other binding groups. Examples of these are markers which distinguish CD4 and CD8 lymphocytes from the general population of lymphocytes. The method of this invention is not adversely affected by the presence of red blood cells in fields of view in the blood sample which are being scanned, and thus does not require significant sample preparation, such as dilutions or gravimetric separation of various cell types.

Since many changes and variations of the disclosed embodiments of the invention may be made without departing from the inventive concept, it is not intended to limit the invention otherwise than as required by the appended claims.

What is claimed is:

1. A method for performing a differential white blood cell count in a sample of anticoagulated whole blood which is contained in a sampling chamber, said method comprising:
   a) the step of providing an admixture of at least one fluorescent colorant and anticoagulated whole blood in said sampling chamber, said colorant being operable to differentially highlight different white blood cell types in the whole blood;
   b) the step of allowing the admixture to disperse through said chamber so as to form red blood cell aggregates which are associated with quiescent groups of one or more individual white blood cells in optical working fields in the sample;
   c) the step of optically performing a multi-field X-Y-Z scan of the dispersed admixture in said chamber under suitable lighting conditions that will cause different white blood cell types to be differentially highlighted by said colorant;
   d) the step of photometrically and/or morphometrically separating different white blood cell sub-populations into distinct clusters, which sub-population clusters include lymphocytes, monocytes, granulocytes, eosinophils and basophils, so as to differentiate the sub-populations of white blood cells which are detected in said scanning step;
   e) the step of enumerating and categorizing the white blood cells in each sub-population cluster; and
   f) the step of deriving a differential count of each of the different sub-populations of white blood cells in each cluster produced by said separating step.

2. The method of claim 1, wherein said chamber is provided with a varying through-plane, or Z axis, thickness which varies from a minimum of about zero to about ten microns to a maximum of about twenty to about fifty microns in the area of said chamber in which said scanning steps are performed.

3. A method for performing a differential nucleated blood cell count in a sample of anticoagulated whole blood which is contained in a sampling chamber having a varying through plane thickness, said method comprising:
   a) the step of providing an admixture of at least one fluorescent colorant and anticoagulated whole blood in said sampling chamber, said colorant being operable to differentially highlight different nucleated blood cell types in the whole blood;
   b) the step of optically performing a multi-field X-Y-Z scan of the admixture in said chamber under suitable lighting conditions that will cause different nucleated cell types to be differentially highlighted by said colorant;
   c) the step of photometrically and/or morphometrically separating at least one nucleated blood cell sub-population into a distinct cluster, wherein said at least one sub-population cluster is one of lymphocytes, monocytes, granulocytes, eosinophils or basophils, so as to differentiate that sub-population of nucleated blood cells from other nucleated cells which are detected in said scanning step;
   d) the step of enumerating and categorizing the nucleated blood cells in said nucleated blood cell sub-population cluster; and
   e) the step of producing a cell count of at least one of the sub-populations of nucleated blood cells in at least one cluster produced by said separating step.

4. A method for performing a reticulocyte count in a substantially undiluted quiescent sample of anticoagulated whole blood which is admixed with one or more fluorescent colorants that are operable to differentially highlight remnants of nucleated material in the reticulocytes in the blood sample, said blood sample and colorants being contained in a viewing chamber having varying thickness regions therein, said method comprising:
   a) the step of scanning the blood sample with an optical instrument having a field of view;
   b) the step of locating fields of view in said quiescent blood sample which fields of view contain individual red cells or monolayers of red cells;
   c) the step of illuminating said located fields of view in the quiescent blood sample with selected wavelengths of light so as to differentially highlight any remnants of nucleated material in red cells in said located fields of view; and
   d) the step of enumerating any differentially highlighted red cells in said fields of view.

5. A method for performing a differential white blood cell count on a substantially undiluted quiescent sample of anticoagulated whole blood which is admixed with one or more fluorescent colorants that are operable to differentially highlight nucleated material in the white cells in the blood sample, said blood sample and colorants being contained in a viewing chamber having varying thickness regions therein, said method comprising:
   a) the step of scanning the blood sample with an optical instrument having a field of view;
   b) the step of locating and scanning fields of view in said quiescent blood sample which fields of view contain individual white blood cells and aggregates of red blood cells, and which fields of view have a viewing chamber through plane thickness of about fifty microns or less;
   c) the step of illuminating said fields of view in the quiescent blood sample with selected wavelengths of light so as to differentially highlight any nucleated material in white blood cells in said located fields of view; and
   d) the step of categorizing and enumerating all differentially highlighted white blood cells in said located and scanned fields of view so as to obtain differential white blood cell counts, said categorizing step being based on differences in light emissions emanating from said differentially highlighted white blood cells.

6. The method of claim 5 wherein said colorant is operable to differentiate types of white cells one from another by reason of different signal characteristics emanating from various types of white cells, whereby a differential white cell count can be derived from said blood sample.

7. The method of claim 5 wherein said categorizing step involves the use of both photometric and morphometric cell information obtained from said differences in light emissions.

8. A method for performing a differential white cell count in a substantially undiluted quiescent sample of anticoagulated whole blood which is admixed with one or more fluorescent colorants that are operable to differentially highlight intracellular dye-binding material in the white cells in the blood sample, said blood sample and colorants being contained in a viewing chamber having varying through plane thickness regions therein, said method comprising:

a) the step of locating usable fields of view having a through plane thickness of less than about fifty microns in said quiescent blood sample which contain at least a predetermined number of individual white blood cells which are separated from aggregates of red blood cells;
   b) the step of illuminating said usable fields of view with at least one predetermined wavelength of light that will differentially highlight intracellular dye-binding material contained in white blood cells and will cause illuminated white blood cells to emit light;
   c) the step of measuring emitted light from said illuminated white blood cells in two or more different wavelengths; and
   d) the step of analyzing said different wavelengths of emitted light in a manner which will differentiate types of white blood cells from each other.

9. The method of claim 8 wherein said differentiating step is performed by using photometric information and/or morphometric information derived from said emitted light, and further including the step of counting such differentiated types of white blood cells.

10. A method for identifying at least one sub-population of target cells containing nucleated material or containing intracellular remnants of nucleated material, which target cells are contained in a substantially undiluted quiescent sample of anticoagulated whole blood that is admixed with a fluorescent colorant, and which is dispersed in a viewing chamber-that includes a region that contains individually separated cells, said region having a through plane thickness that is in the range of about zero microns to about forty microns, said method comprising:

a) the step of optically scanning selected fields of view in said region which fields contain individual red blood cells, and/or monolayers of red blood cells, and/or red blood cell aggregates;
   b) the step of illuminating said selected fields of view with a light source of one or more preselected wavelengths operable to cause said fluorescent colorant to produce nucleated material or remnant nucleated material fluorescent emissions of a plurality of known wavelengths, which emissions are characteristic of sub-populations of cells; and
   c) the step of analyzing said emissions at said plurality of known wavelengths so as to identify the sub-populations of cells in the fields of view.

11. The method of claim 10 wherein the viewing chamber includes additional regions which have a through plane thickness which is greater than about forty microns.

12. The method of claim 10 wherein the colorant is a supravital stain.

13. The method of claim 10 wherein the sub-population of target cells is a sub-population of white blood cells.

14. The method of claim 10 wherein the sub-population of target cells is a sub-population of red blood cells.

15. The method of claim 10 wherein the colorant is part of a binding particle that is directed against an epitope on the sub-population of target cells.

16. The method of claim 10 wherein said emissions are characterized by photometric and/or morphometric characteristics which can be used to identify the sub-population in question.

17. A method for identifying at least one sub-population of nucleated blood cells which are contained in a substantially undiluted quiescent sample of anticoagulated whole blood that is admixed with a fluorescent colorant and is dispersed in a viewing chamber that includes a region that contains aggregates of red blood cells, and individually separated nucleated cells, said region having a through plane thickness which is no greater than about fifty microns, said method comprising:

a) the step of scanning selected fields of view in said region with an optical scanning instrument;
   b) the step of illuminating said selected fields of view with a light source of a preselected wavelength that is operable to cause said fluorescent colorant to produce fluorescent emissions at a plurality of known wavelengths, which emissions are characteristic of sub-populations of nucleated cells; and
   c) the step of analyzing said emissions at said plurality of known wavelengths so as to identify any sub-populations of nucleated cells in the fields of view.

18. A method of identifying sub-populations of nucleated cells contained in a substantially undiluted quiescent sample of anticoagulated whole blood which is admixed with a fluorescent colorant and which is dispersed in a viewing chamber that includes a region that contains individually separated nucleated cells, said region having a through plane thickness that is no greater than about fifty microns, said method comprising:

a) the step of scanning selected fields of view in said region with an optical scanning instrument;
   b) the step of illuminating said selected fields of view with a light source of a preselected wavelength that is operable to cause said fluorescent colorant to produce fluorescent emissions at a plurality of known wavelengths, which emissions are characteristic of a sub-population of nucleated cells; and
   c) the step of analyzing said emissions at said plurality of known wavelengths so as to identify the sub-population of nucleated cells in the fields of view.

19. A method of identifying target sub-populations of nucleated cells contained in a substantially undiluted quiescent sample of anticoagulated whole blood which is admixed with a fluorescent colorant, and which is dispersed in a viewing chamber that includes a region that contains individual red blood cells, and/or monolayers of red blood cells, and/or aggregates of red blood cells, and which region has a through plane thickness that is no greater than about fifty microns, said method comprising:

a) the step of scanning selected fields of view in said region with an optical scanning instrument;
   b) the step of illuminating said selected fields of view with a light source of one or more preselected wavelengths that are operable to cause said fluorescent colorant to produce fluorescent emissions at one or more known wavelengths, which emissions are characteristic of said target sub-populations of nucleated cells; and
   c) the step of analyzing said emissions at said known wavelengths so as to identify and differentiate said target sub-populations of nucleated cells.

20. The method of claim 19 wherein said viewing chamber is substantially wedge-shaped and includes additional regions which have through plane thicknesses that are greater than about forty microns.

21. A method of identifying reticulocyte cells contained in a substantially undiluted quiescent sample of anticoagulated whole blood which is admixed with a fluorescent colorant, and which is dispersed in a viewing chamber that includes a region that contains individual red blood cells, and/or monolayers of red blood cells, and which region has a through plane thickness that is no greater than about twenty microns, said method comprising:

a) the step of scanning selected fields of view in said region with an optical scanning instrument;

b) the step of illuminating said selected fields of view with a light source of one or more preselected wavelengths that are operable to cause said fluorescent colorant to produce fluorescent emissions at one or more known wavelengths, which emissions are characteristic of remnants of nucleated material contained in said reticulocyte cells; and c) the step of analyzing said emissions at said known wavelengths so as to identify and differentiate said reticulocyte cells from other cells in said selected fields of view in the sample.

22. A method for performing a reticulocyte count in a substantially undiluted quiescent sample of anticoagulated whole blood which is admixed with one or more fluorescent colorants that are operable to differentially highlight remnants of nucleated material in the reticulocytes in the blood sample, said blood sample and colorants being contained in a viewing chamber, said method comprising:

a) the step of scanning the blood sample with an optical instrument having a field of view;

b) the step of locating fields of view in said quiescent blood sample which fields of view contain individual red cells or monolayers of red cells;

c) the step of illuminating said located fields of view in the quiescent blood sample with selected wavelengths of light so as to differentially highlight any remnants of nucleated material in red cells in said located fields of view; and d) the step of enumerating any differentially highlighted red cells in said fields of view.

23. A method of identifying target sub-populations of cells or other formed bodies contained in a substantially undiluted quiescent sample of anticoagulated whole blood which is admixed with a fluorescent colorant, and which is dispersed in a viewing chamber that includes a region that contains individual red blood cells, and/or monolayers of red blood cells, and/or aggregates of red blood cells, said method comprising:

a) the step of scanning selected fields of view in said region with an optical scanning instrument, which selected fields of view have a through plane thickness of about fifty microns or less;

b) the step of illuminating said selected fields of view with a light source of one or more preselected wavelengths that are operable to cause said fluorescent colorant to produce fluorescent emissions at one or more known wavelengths, which emissions produce photometric and morphometric information which are operable to differentiate said target sub-populations of cells and other formed bodies; and c) the step of analyzing said emissions so as to identify and differentiate said target sub-populations of cells and formed bodies both photometrically and morphometrically.

* * * * *